United States Patent
Zhang et al.

(10) Patent No.: US 11,214,656 B2
(45) Date of Patent: Jan. 4, 2022

(54) PREPARATION METHOD OF CROSS-LINKED SODIUM HYALURONATE GEL

(71) Applicants: Hangzhou Singclean Medical Products Co., Ltd, Zhejiang (CN); Zhejiang University of Science and Technology, Zhejiang (CN)

(72) Inventors: Zhiguo Zhang, Zhejiang (CN); Yange Suo, Zhejiang (CN); Wei Huang, Zhejiang (CN); Weiqing Sun, Zhejiang (CN)

(73) Assignees: Hangzhou Singclean Medical Products Co., Ltd, Hangzhou (CN); Zhejiang University of Science and Technology, Hangzhou (CN)

( * ) Notice: Subject to any disclaimer, the term of this patent is extended or adjusted under 35 U.S.C. 154(b) by 0 days.

(21) Appl. No.: 16/729,467

(22) Filed: Dec. 29, 2019

(65) Prior Publication Data
US 2020/0407516 A1    Dec. 31, 2020

(30) Foreign Application Priority Data

Jun. 28, 2019   (CN) .......................... 201910572212.X

(51) Int. Cl.
*C08J 3/075* (2006.01)
*C08J 3/24* (2006.01)
*A61L 27/20* (2006.01)

(52) U.S. Cl.
CPC ............... *C08J 3/075* (2013.01); *A61L 27/20* (2013.01); *C08J 3/24* (2013.01); *A61L 2430/40* (2013.01); *C08J 2305/08* (2013.01)

(58) Field of Classification Search
CPC ... C08J 3/075; C08J 3/24; A61L 27/20; A61L 2430/40

USPC .......................................................... 536/124
See application file for complete search history.

(56) References Cited

U.S. PATENT DOCUMENTS 7,829,118 B1 * 11/2010 Gravett .................... A61K 9/10
                                                    424/488
2011/0262489 A1 * 10/2011 Zhao .................... A61K 9/0021
                                                    424/400

OTHER PUBLICATIONS

Labconco: A Guide To Freeze Drying for the Laboratory. 2004 by Labconco Corporation, pp. 1-12. (Year: 2004).*

* cited by examiner

*Primary Examiner* — Yih-Horng Shiao

(57) ABSTRACT

A preparation method of a cross-linked sodium hyaluronate gel is disclosed, which including: preparing an alkaline aqueous solution of hyaluronic acid: formulating a sodium hyaluronate alkali liquor with the concentration of 10-30% g/ml; and carrying out a cross-linking reaction: the cross-linking agent used in the cross-linking reaction being divinyl sulfone or 1,4-butanediol diglycidyl ether, the cross-linking reaction being carried out in an alkaline aqueous solution of hyaluronic acid, the reaction temperature of the cross-linking reaction being 20-40° C., the time of the cross-linking reaction being 4-8 h, and the like. The method of this invention has many advantages, such as easily available raw materials, mild reaction conditions, high cross-linking efficiency, simple process and post-treatment, and easy operation. The obtained cross-linked sodium hyaluronate has a three-dimensional network structure by the crosslinking reaction with good mechanical properties, and can be used as a good drug carrier and a tissue engineering scaffold material.

7 Claims, No Drawings

PREPARATION METHOD OF CROSS-LINKED SODIUM HYALURONATE GEL

CROSS REFERENCE TO RELATED APPLICATION

The present application claims the benefit of Chinese Patent Application No. 201910572212.X filed on Jun. 28, 2019, the contents of which are incorporated herein by reference in their entirety.

FIELD OF THE INVENTION

The invention relates to the technical field of polymer materials, and particularly relates to a preparation method of a cross-linked sodium hyaluronate gel.

BACKGROUND OF THE INVENTION

Hyaluronic acid (HA), also known as hyaluronic acid, is one of the most representative mucopolysaccharides widely distributed in various parts of the human body, showing a variety of important physiological functions in the body due to its unique molecular structure and physicochemical properties, such as lubrication of joints, regulation of vascular permeability, regulation of protein, diffusion and transportion of water-electrolyte, promotion of wound healing. Hyaluronic acid was firstly isolated from bovine vitreous for the first time, it is widely found in the extracellular matrix of human connective tissues, as a linear polysaccharide composed of repeating disaccharide units of D-glucuronic acid and N-acetylglucosamine linked by β1-3 bond and β1-4 bond alternately. Hyaluronic acid has no species and tissue specificity, showing good histocompatibility and inducing little immune response in vivo. Hyaluronic acid is highly hydrophilic, which physicochemical property enables hyaluronic acid to maintain gelatinous even at a very low concentration, hyaluronic acid increases in volume after absorbing water, and generates expansion pressure to the periphery so that hyaluronic acid can support surrounding tissues. However, natural hyaluronic acid has a half-life period of only 1-2 days in tissues and is decomposed into $CO_2$ and $H_2O$ by hyaluronidase or oxygen free radicals in the liver.

In order to prolong the residence time of hyaluronic acid in vivo, an improvement in mechanical strength and a decrease in the degradation rate of hyaluronic acid are usually achieved by means of modification or crosslinking. At present, the commonly used crosslinking agents are divinyl sulfone and 1,4-butanediol diglycidyl ether, and the degradation time of hyaluronic acid can only be adjusted by the degree of crosslinking. Therefore, it is difficult to implement clinically, especially as a tissue engineering scaffold material with controllable degradation.

Cross-linked sodium hyaluronate is one of cross-linked HA derivatives, which is a gel macromolecule, also known as a cross-linked sodium hyaluronate gel, formed by a crosslinking reaction of the sugar ring active group on cross-linked sodium hyaluronate with a crosslinking agent under certain conditions. A crosslinking reaction is a complex reaction in which macromolecules contain multiple sites in space. The physicochemical properties of cross-linked sodium hyaluronate are closely related to the degree of crosslinking. The cross-linked hyaluronic acid particles prepared currently have a uniform particle size distribution and a high water swelling ratio, but most of them are distributed at the nanometer level, which is suitable for improving the absorption capacity of skin tissues, but unsuitable for interventional embolization treatment. In addition, during the primary crosslinking reaction in the aqueous phase, the crosslinking agent cannot be uniformly dispersed among hyaluronic acid molecules, causing a non-uniform overall crosslinking degree. In summary, the cross-linked sodium hyaluronate gel currently still lacks a more effective cross-linking means to achieve the goal of being used as a tissue engineering scaffold material.

SUMMARY OF THE INVENTION

The technical problem to be solved by the invention is to provide a preparation method of a cross-linked sodium hyaluronate gel, and therefore the invention adopts the following technical solutions:

The invention discloses a preparation method of a cross-linked sodium hyaluronate gel, which comprising the following preparation steps:

1) preparing an alkaline aqueous solution of hyaluronic acid: formulating an alkali liquor of sodium hyaluronate with a concentration of 10-30% g/ml;

2) performing a crosslinking reaction, wherein a crosslinking agent used in the crosslinking reaction is divinyl sulfone or 1,4-butanediol diglycidyl ether, the crosslinking reaction is carried out in the alkaline aqueous solution of hyaluronic acid, the reaction temperature of the crosslinking reaction is in a range from 20° C. to 40° C., and the time of the crosslinking reaction is 4-8 h;

3) freeze-drying: after the crosslinking reaction being finished, dialyzing and freeze-drying to obtain a cross-linked sodium hyaluronate gel dry glue, the dialysis phosphate buffer preferably having a phosphate concentration of 0.1-0.2 M and a pH of 7.0-7.4;

4) performing a secondary reaction: adding the dried gel dry glue into a certain amount of prepared ammonium persulfate or potassium persulfate aqueous solution with a mass fraction of 1-5%, after fully soaking and swelling, heating to 50-70° C. and maintaining the reaction for 2-6 h;

5) preparing a gel: after the secondary reaction being finished, soaking and washing with a large amount of aqueous ethanol, and finally soaking and swelling with a phosphate buffer solution at pH 7.4 to obtain a crosslinked sodium hyaluronate gel.

As a further improvement, the mass ratio of the hyaluronic acid to the crosslinking agent according to the present invention is 5-20:1.

As a further improvement, the freeze-drying process of the present invention comprises: a first stage of pre-freezing at −65° C. to −45° C. for 2-6 h, a second stage of sublimation at −30° C. to −25° C. for 4-8 h and at −10° C. to 0° C. for 3-8 h, and a third stage of analytical drying at 5° C. to 25° C. for 3-8 h.

The invention also discloses a use of the cross-linked sodium hyaluronate gel prepared by the present preparation method of the cross-linked sodium hyaluronate gel in a tissue engineering scaffold.

The invention has the beneficial effects as follows:

In the prior art, in order to obtain the cross-linked sodium hyaluronate gel, the gel is mostly prepared by diluting a solution to homogenize the system, then concentrating, and standing the reaction, and finally cutting and crushing. The obtained product has many disadvantages, such as poor gel strength, undesired homogeneity, local agglomeration, non-uniform crosslinking and irregular particles, and poor rheology.

The preparation method of the cross-linked sodium hyaluronate gel provided by the invention has many advantages, such as easily available raw materials, mild reaction conditions, high cross-linking efficiency, simple process and post-treatment, and easy operation. The obtained cross-linked sodium hyaluronate has a three-dimensional network structure by the crosslinking reaction with good mechanical properties, and can be used as a good drug carrier and a tissue engineering scaffold material.

More importantly, according to the invention, after the hyaluronic acid is subjected to a primary crosslinking reaction to obtain the sodium hyaluronate gel, ammonium persulfate or potassium persulfate aqueous initiator is further used to carry out a deep crosslinking, during which the remaining crosslinking reaction sites which are difficult to crosslink are subjected to a thorough crosslink initiated by ammonium persulfate or potassium persulfate, thereby largely improving the degree of crosslinking as well as the mechanical strength of the gel product, thus allowing the product to be used as a tissue engineering scaffold material. By investigation, it has been found that the dehydration crosslinking reaction between polymer systems is promoted by the initiation of ammonium persulfate or potassium persulfate. By fully swelling and subsequent crosslinking in an aqueous solution of ammonium persulfate or potassium persulfate, the crosslinking of the final product is uniform and thorough, thereby improving the application performance of the product.

DETAILED DESCRIPTION OF THE EMBODIMENTS

Examples of the present invention are given below to further explain the present invention in detail, but the present invention is not limited thereto.

Example 1

(1) Preparing an alkaline aqueous solution of hyaluronic acid: hyaluronic acid 10.00 g (a molecular weight of 900,000-1,100,000) was formulated into an alkali liquor of sodium hyaluronate at a concentration of 10% g/ml.

(2) Crosslinking reaction. The crosslinking agent used in the crosslinking reaction was divinyl sulfone in an amount of 2.00 g. The crosslinking reaction is carried out in the alkaline aqueous solution of hyaluronic acid. The reaction temperature of the crosslinking reaction was 20° C. The crosslinking reaction time was 4 h.

(3) Freeze-drying. After the crosslinking reaction being finished, dialyzing and freeze-drying to obtain the cross-linked sodium hyaluronate gel dry glue. The dialysis phosphate buffer preferably has a phosphate concentration of 0.1 M and a pH of 7.0. The freeze-drying procedure comprises: a first stage of pre-freezing at −65° C. to −45° C. for 2 h, a second stage of sublimation at −30° C. to −25° C. for 4 h and at −10° C. to 0° C. for 3 h, and a third stage of analytical drying at 5° C. to 25° C. for 3 h.

(4) Secondary reaction. The dried gel dry glue was added into 200 ml of a prepared ammonium persulfate aqueous solution with a mass fraction of 1%. After fully soaking and swelling, the mixture was heated to 50° C. The reaction was maintained for 2 h.

(5) Gel preparation. After the reaction being finished, the product was washed by soaking with a large amount of aqueous ethanol. And finally soaking and swelling with a phosphate buffer solution at pH 7.4 to obtain the crosslinked sodium hyaluronate gel.

The cross-linked sodium hyaluronate gel prepared in the example has a maximum tensile strength up to 0.5 MPa by testing, and thus can be used for tissue engineering scaffolds and shows a high mechanical strength.

Example 2

(1) Preparing an alkaline aqueous solution of hyaluronic acid: hyaluronic acid 10.00 g (a molecular weight of 900,000-1,100,000) was formulated into an alkaline liquor of sodium hyaluronate at a concentration of 30% g/ml.

(2) Crosslinking. The crosslinking agent used in the crosslinking reaction was 1,4-butanediol diglycidyl ether in an amount of 0.50 g. The crosslinking reaction was carried out in the alkaline aqueous solution of hyaluronic acid. The reaction temperature of the crosslinking reaction was 40° C. The crosslinking reaction time was 8 h.

(3) Freeze-drying. After the crosslinking reaction being finished, the product was dialyzed and freeze-dryed to obtain the cross-linked sodium hyaluronate gel dry glue. The dialysis phosphate buffer preferably has a phosphate concentration of 0.2 M and a pH of 7.4. The freeze-drying procedure comprises: a first stage of pre-freezing at −65° C. to −45° C. for 6 h, a second stage of sublimation at −30° C. to −25° C. for 8 h and at −10° C. to 0° C. for 8 h, and a third stage of analytical drying at 5° C. to 25° C. for 8 h.

(4) Secondary reaction. The gel dry glue dried as above was added into 100 ml of a prepared potassium persulfate aqueous solution with a mass fraction of 5%, after fully soaking and swelling, the mixture was heated to 70° C. The reaction was maintained for 6 h.

(5) Gel preparation. After the reaction being finished, the product was washed by soaking with a large amount of aqueous ethanol. And finally soaking and swelling with a phosphate buffer solution at pH 7.4 to obtain the crosslinked sodium hyaluronate gel.

The cross-linked sodium hyaluronate gel prepared in the example has a maximum tensile strength up to 0.8 MPa by testing, thus can be used for tissue engineering scaffolds and shows a high mechanical strength.

Example 3

(1) Preparing an alkaline aqueous solution of hyaluronic acid: hyaluronic acid 10.00 g (a molecular weight of 1,700,000-1,900,000) was formulated into an alkaline liquor of sodium hyaluronate at a concentration of 20% g/ml.

(2) Crosslinking reaction. The crosslinking agent used in the crosslinking reaction was divinyl sulfone in an amount of 1.00 g. The crosslinking reaction was carried out in the alkaline aqueous solution of hyaluronic acid. The reaction temperature of the crosslinking reaction was 30° C. The crosslinking reaction time was 6 h.

(3) Freeze-drying. After the crosslinking reaction being finished, the product was dialyzed and freeze-dryed to obtain the cross-linked sodium hyaluronate gel dry glue. The dialysis phosphate buffer preferably has a phosphate concentration of 0.15 M and a pH of 7.2. The freeze-drying procedure comprises: a first stage of pre-freezing at −65° C. to −45° C. for 5 h, a second stage of sublimation at −30° C. to −25° C. for 7 h and at −10° C. to 0° C. for 7 h, and a third stage of analytical drying at 5° C. to 25° C. for 7 h.

(4) Secondary reaction. The gel dry glue dried as above was added into 150 ml of a prepared ammonium persulfate aqueous solution with a mass fraction of 3%, after fully soaking and swelling, the mixture was heated to 60° C. The reaction was maintained for 4 h.

(5) Gel Preparation. After the reaction being finished, the product was washed by soaking with a large amount of aqueous ethanol. And finally soaking and swelling with a phosphate buffer solution at pH 7.4 to obtain the cross-linked sodium hyaluronate gel.

The cross-linked sodium hyaluronate gel prepared in the example has a maximum tensile strength up to 2.95 MPa after testing, and can be used for tissue engineering scaffolds and shows a high mechanical strength.

Example 4

(1) Preparing an alkaline aqueous solution of hyaluronic acid: hyaluronic acid 10.00 g (a molecular weight of 1,700,000-1,900,000) was formulated into an alkaline liquor of sodium hyaluronate at a concentration of 15% g/ml.

(2) Crosslinking reaction. The crosslinking agent used in the crosslinking reaction was 1,4-butanediol diglycidyl ether in an amount of 1.00 g. The crosslinking reaction was carried out in the alkaline aqueous solution of hyaluronic acid. The reaction temperature of the crosslinking reaction was 30° C. The crosslinking reaction time was 7 h.

(3) Freeze-drying. After the crosslinking reaction being finished, the product was dialyzed and freeze-dryed to obtain the cross-linked sodium hyaluronate gel dry glue. The dialysis phosphate buffer preferably has a phosphate concentration of 0.2 M and a pH of 7.4. The freeze-drying procedure comprises: a first stage of pre-freezing at −65° C. to −45° C. for 6 h, a second stage of sublimation at −30° C. to −25° C. for 8 h and −10° C. to 0° C. for 8 h, and a third stage of analytical drying at 5° C. to 25° C. for 8 h.

(4) Secondary reaction. The gel dry glue dried as above was added into 200 ml of a prepared potassium persulfate aqueous solution with a mass fraction of 3.5%, after fully soaking and swelling, the mixture was heated to 55° C. The reaction was maintained for 5 h.

(5) Gel Preparation. After the reaction being finished, the product was washed by soaking with a large amount of aqueous ethanol. And finally soaking and swelling with a phosphate buffer solution at pH 7.4 to obtain the crosslinked sodium hyaluronate gel.

The crosslinked sodium hyaluronate gel prepared in the example has a maximum tensile strength of 3.20 MPa, thus can be used for tissue engineering scaffolds and shows a high mechanical strength.

Finally, it should also be noted that the above listed are only specific examples of the present invention. Obviously, the present invention is not limited to the above examples, but many variations are possible. All variations which may be derived or associated by those skilled in the art from this disclosure are to be considered within the scope of this invention.

The invention claimed is:

1. A method for preparing cross-linked sodium hyaluronate gel, comprising the following steps:
    1) preparing an alkaline aqueous solution of hyaluronic acid: formulating an alkali liquor of sodium hyaluronate with a concentration of 10-30% g/ml;
    2) performing a crosslinking reaction by adding a crosslinking agent to the alkaline aqueous solution of hyaluronic acid, wherein the cross-linking agent used in the crosslinking reaction is divinyl sulfone or 1,4-butanediol diglycidyl ether, wherein the reaction temperature of the crosslinking reaction is in a range from 20° C. to 40° C., and the time of the crosslinking reaction is 4-8 h, wherein the crosslinking reaction results in a cross-linked sodium hyaluronate glue;
    3) dialyzing and freeze-drying: after the crosslinking reaction being finished, dialyzing the cross-linked sodium hyaluronate glue in a phosphate buffer and freeze-drying to obtain a cross-linked sodium hyaluronate dry glue, wherein the phosphate buffer for the dialyzing step has a phosphate concentration of 0.1-0.2 M and a pH of 7.0-7.4;
    4) performing a secondary reaction consisting of adding the cross-linked sodium hyaluronate dry glue into a prepared ammonium persulfate or potassium persulfate aqueous solution having a mass fraction of 1-5%, after fully soaking and swelling the cross-linked sodium hyaluronate dry glue in the ammonium persulfate or potassium persulfate aqueous solution, heating the ammonium persulfate or potassium persulfate aqueous solution to 50-70° C. to allow a secondary cross-linking reaction to occur and maintaining the secondary cross-linking reaction for 2-6 h to result in a secondary reaction product;
    5) preparing a gel: after the secondary reaction being finished, soaking and washing the secondary reaction product with aqueous ethanol, and finally soaking and swelling the secondary reaction product with a phosphate buffer solution at pH 7.4 to obtain the crosslinked sodium hyaluronate gel.

2. The method according to claim 1, wherein the mass ratio of hyaluronic acid to the crosslinking agent is 5-20:1.

3. The method according to claim 1, wherein the freeze-drying step comprises: 1) pre-freezing at −65° C. to −45° C. for 2-6 h; 2) sublimation at −30° C. to −25° C. for 4-8 h and subsequently at −10° C. to 0° C. for 3-8 h; and 3) drying at 5° C. to 25° C. for 3-8 h.

4. The method according to claim 2, wherein the freeze-drying step comprises: 1) pre-freezing at −65° C. to −45° C. for 2-6 h; 2) sublimation at −30° C. to −25° C. for 4-8 h and subsequently at −10° C. to 0° C. for 3-8 h; and 3) drying at 5° C. to 25° C. for 3-8 h.

5. A tissue engineering scaffold comprising a cross-linked sodium hyaluronate gel prepared by the method according to claim 1.

6. A tissue engineering scaffold comprising a cross-linked sodium hyaluronate gel prepared by the method according to claim 2.

7. The method of claim 1, wherein the amount of ammonium persulfate or potassium persulfate aqueous solution used at step 4) is 100, 150, or 200 ml.

\* \* \* \* \*